(12) United States Patent
Rasmussen et al.

(10) Patent No.: US 8,833,402 B2
(45) Date of Patent: Sep. 16, 2014

(54) WOVEN FABRIC HAVING COMPOSITE YARNS FOR ENDOLUMINAL DEVICES

(75) Inventors: Erik E. Rasmussen, Slagelse (DK);
William Kurt Dierking, Louisville, KY (US); Matthew S. Huser, West Lafayette, IN (US); Shyam Kuppurathanam, Bloomington, IN (US); Jarin Kratzberg, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/331,944

(22) Filed: Dec. 20, 2011

(65) Prior Publication Data
US 2012/0168022 A1 Jul. 5, 2012

Related U.S. Application Data

(60) Provisional application No. 61/428,580, filed on Dec. 30, 2010.

(51) Int. Cl.
*D03D 3/02* (2006.01)
*D03D 25/00* (2006.01)

(52) U.S. Cl.
USPC ............... 139/387 R; 139/384 R; 139/420 R; 139/426 R; 139/420 A

(58) Field of Classification Search
CPC ....... A61F 2/07; A61F 2002/075; A61F 2/90; A61F 2/88; A61F 2/89; A61F 2002/065; A61F 2/06; A61F 2002/072; A61F 2220/0075; A61F 2002/9511; A61F 2230/0067; A61F 2/92; A61F 2250/0028; A61F 2210/0076; A61F 2240/001; A61F 2/856; A61F 2/962; A61L 17/105; A61L 29/106; C08L 23/06; C08L 67/02; C08L 67/04; C08L 2203/12; C08L 67/00; C08L 23/00; C08L 71/00; C08L 2207/068; A61B 17/06166; A61B 2017/0619; A61B 17/842; A61B 2017/00526; D02G 3/38; D02G 3/448; D02G 3/449; D02G 3/185; D07B 2205/2014; D07B 2801/10; D07B 1/025; D07B 2201/1096; D10B 2509/06; D10B 2231/04; D10B 2321/02; D10B 2321/021; D10B 2321/0211; D10B 2401/063; D10B 2403/0114; D10B 2509/00; D10B 2509/04; D03D 3/02; D03D 13/008; D03D 15/00; D03D 15/0027; D03D 15/08; D03D 1/00; D04B 21/00; D04B 1/16; D04B 21/14; D04B 9/44; D04C 1/12; D04C 1/06; A61M 25/10; Y10S 623/901
USPC ....... 139/383 R, 384 R, 387 R, 420 R, 426 R, 139/420 A
See application file for complete search history.

(56) References Cited

U.S. PATENT DOCUMENTS 3,775,961 A * 12/1973 Womer .......................... 57/310
3,998,988 A * 12/1976 Shimomai et al. ............ 428/400

(Continued)

FOREIGN PATENT DOCUMENTS

EP 0128741 9/1987
EP 2136858 11/2010

(Continued)

OTHER PUBLICATIONS

European Search Report, EP 11275166, filed Dec. 21, 2011, search completed Apr. 17, 2013.

(Continued)

*Primary Examiner* — Bobby Muromoto, Jr.
(74) *Attorney, Agent, or Firm* — Brinks Gilson & Lione

(57) ABSTRACT

A woven fabric for a low profile implantable medical device includes a plurality of textile strands of a composite yarn aligned in a first direction interlaced with a plurality of textile strands of the composite yarn aligned in a second direction. The composite yarn includes a combination of a first material and a second material. The textile strands have a size between about 10 denier to about 20 denier. The first material has at least one characteristic different from the second material and the second material reacts favorably with blood when placed within an artery.

16 Claims, 3 Drawing Sheets

(56) References Cited

U.S. PATENT DOCUMENTS

| | | | |
|---|---|---|---|
| 4,743,250 A * | 5/1988 | Kitagawa et al. | 128/898 |
| 5,236,447 A * | 8/1993 | Kubo et al. | 623/1.13 |
| 5,476,506 A * | 12/1995 | Lunn | 623/1.28 |
| 5,674,276 A * | 10/1997 | Andersen et al. | 623/1.5 |
| 5,873,904 A * | 2/1999 | Ragheb et al. | 623/1.13 |
| 5,876,432 A * | 3/1999 | Lau et al. | 623/1.13 |
| 5,957,974 A * | 9/1999 | Thompson et al. | 623/1.13 |
| 6,042,605 A * | 3/2000 | Martin et al. | 623/1.13 |
| 6,155,084 A * | 12/2000 | Andrews et al. | 66/174 |
| 6,187,036 B1 * | 2/2001 | Shaolian et al. | 623/1.15 |
| 6,364,901 B1 | 4/2002 | Inoue | |
| 6,517,572 B2 * | 2/2003 | Kugler et al. | 623/1.13 |
| 6,645,242 B1 * | 11/2003 | Quinn | 623/1.16 |
| 6,814,754 B2 * | 11/2004 | Greenhalgh | 623/1.51 |
| 6,984,243 B2 | 1/2006 | Dwyer et al. | |
| 7,029,490 B2 * | 4/2006 | Grafton et al. | 606/228 |
| 7,121,077 B2 * | 10/2006 | Andrews et al. | 57/210 |
| 8,074,436 B2 * | 12/2011 | Hardee et al. | 57/224 |
| 2002/0193820 A1 * | 12/2002 | Wakuda et al. | 606/194 |
| 2003/0023241 A1 * | 1/2003 | Drewry et al. | 606/61 |
| 2003/0028239 A1 * | 2/2003 | Dong | 623/1.13 |
| 2003/0050666 A1 * | 3/2003 | Grafton | 606/228 |
| 2003/0125796 A1 * | 7/2003 | Dong | 623/1.13 |
| 2003/0149464 A1 * | 8/2003 | Dong | 623/1.5 |
| 2003/0204241 A1 * | 10/2003 | Dong | 623/1.13 |
| 2004/0187471 A1 * | 9/2004 | Andrews et al. | 57/232 |
| 2004/0267313 A1 * | 12/2004 | Amery et al. | 606/228 |
| 2005/0125036 A1 * | 6/2005 | Roby | 606/228 |
| 2005/0159803 A1 * | 7/2005 | Lad et al. | 623/1.13 |
| 2005/0159804 A1 * | 7/2005 | Lad et al. | 623/1.13 |
| 2005/0222661 A1 * | 10/2005 | Case et al. | 623/1.1 |
| 2005/0240261 A1 | 10/2005 | Rakos et al. | |
| 2006/0009835 A1 * | 1/2006 | Osborne et al. | 623/1.13 |
| 2006/0205308 A1 * | 9/2006 | Kihara | 442/336 |
| 2007/0084182 A1 * | 4/2007 | Andrews et al. | 57/232 |
| 2008/0009903 A1 * | 1/2008 | Schmieding et al. | 606/228 |
| 2009/0024151 A1 * | 1/2009 | Shalaby et al. | 606/154 |
| 2009/0035572 A1 * | 2/2009 | Hotter et al. | 428/373 |
| 2009/0171440 A1 | 7/2009 | Carlson et al. | |
| 2009/0204118 A1 * | 8/2009 | Pratt | 606/74 |
| 2011/0165396 A1 | 7/2011 | Norris et al. | |
| 2012/0168022 A1 * | 7/2012 | Rasmussen et al. | 139/11 |

FOREIGN PATENT DOCUMENTS

| | | |
|---|---|---|
| GB | 1097787 | 1/1968 |
| WO | 99/32051 | 7/1999 |
| WO | 02/28314 | 4/2002 |
| WO | 2008/109019 | 9/2008 |
| WO | 2008/112242 | 9/2008 |
| WO | 2010/139340 | 12/2010 |

OTHER PUBLICATIONS

First Examination Report, AU App. No. 2011265361, report issued Jan. 22, 2013.

Huijing Zhao et al., "In Vitro Fatigue Properties of Prototype Textile Components of Endovascular Devices", Fibers and Polymers 2009, vol. 10, No. 1, 91-97.

Tarng-Jenn yu et al., "Biocomponent vascular grafts consisting of synthetic absorbable fibers. I. In vitro study", Journal of Biomedical Materials Research, vol. 27, 1329-1339 (1993).

Extended European Search Report, EP 11275165, filed Dec. 21, 2011, Apr. 24, 2013.

Australian Patent Examination Report, AU App. No. 2011265360, filed Dec. 20, 2011, Jan. 22, 2013.

* cited by examiner

WOVEN FABRIC HAVING COMPOSITE YARNS FOR ENDOLUMINAL DEVICES

RELATED APPLICATIONS

The present application claims priority to U.S. Provisional Patent Application Ser. No. 61/428,580 filed Dec. 30, 2010, the entirety of which is hereby incorporated by reference.

TECHNICAL FIELD

The present invention relates to woven fabrics. More particularly, the present invention relates low profile woven fabrics for implantable medical devices constructed of at least two different materials having different characteristics.

BACKGROUND

This invention relates generally to medical devices and particularly to medical devices that are implantable within the human or animal body for the repair of damaged vessels, ducts or other physiological passageways and cavities. The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or preserve any remaining vascular integrity by replacing a length of the existing passageway or duct wall that spans the site of failure or defect. Endoluminal prostheses may be of a unitary construction or may be comprised of multiple prosthetic modules.

BRIEF SUMMARY

In one aspect, a woven fabric for a low profile implantable medical device includes a plurality of textile strands of a composite yarn aligned in a first direction interlaced with a plurality of textile strands of the composite yarn aligned in a second direction. The composite yarn includes a combination of a first material and a second material. The textile strands have a size between about 10 denier to about 20 denier. The first material has at least one characteristic different from the second material and the second material reacts favorably with blood when placed within an artery. In some aspects, the textile strands of composite yarn comprise about 50% of the first material by size and about 50% of the second material by size.

In another aspect, a woven fabric suitable for an implantable medical device includes a plurality of textile strands of a composite yarn aligned in a first direction interlaced with a plurality of textile strands of a composite yarn in a second direction. The composite yarn comprises polyester fibers intertwined with polyethylene fibers, the polyester fibers and the polyethylene fibers each having a size of about 10 denier to about 20 denier. The polyester fibers have at least one characteristic different than the polyethylene fibers. In some aspects, the composite yarn is a rope having a central core of polyethylene fibers surrounded by polyester fibers.

In yet another aspect, a method of producing a woven fabric for an implantable medical device is provided. The method comprises providing a plurality of textile strands of a composite yarn to be aligned in a first direction and providing a plurality of textile strands of the composite yarn to be aligned in a second direction. The textile strands are woven together to produce a woven fabric. The textile strands of the composite yarn have a size between about 10 denier to about 20 denier. The composite yarn comprises a combination of a first material and a second material. In some aspects, the weave is a plain weave.

DETAILED DESCRIPTION

Figure 1:
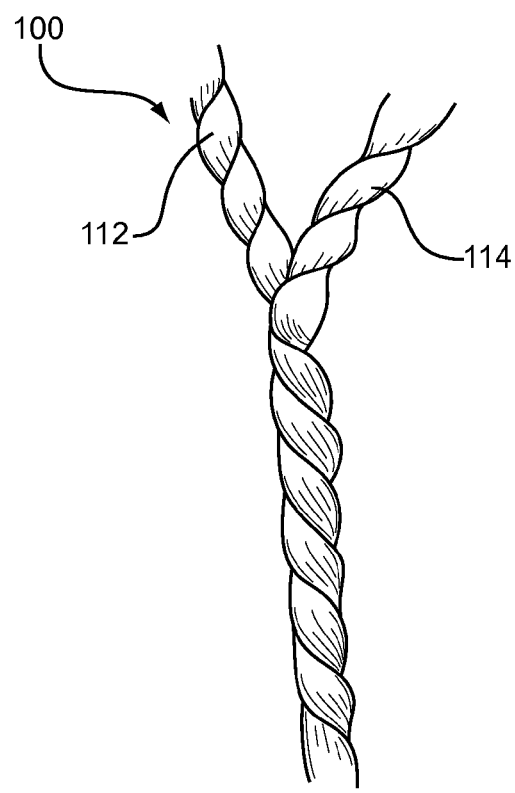
FIG. 1 is an embodiment of a composite yarn formed into a twisted rope.

Unless defined otherwise, all technical and scientific terms used herein have the same meaning as commonly understood to one of ordinary skill in the art to which this invention belongs.

The term "implantable" refers to an ability of a medical device to be positioned at a location within a body, such as within a body lumen.

The term "strand" as used herein is a generic term for a continuous strand of material suitable for weaving. For example, strands may include, but are not limited to monofilaments, filaments twisted together, fibers spun together or otherwise joined, yarns, roving yarns, crepe yarns, ply yarns, cord yarns, threads, strings, filaments laid together without twist, as well as other configurations.

The term "binding point" refers to the intersection of a single strand in a first direction with strands in a second direction. For example, a strand in a first direction may run "over" one or multiple strands in a second direction, have a binding point, and run "under" one or more subsequent strands in the second direction.

The term "float" refers to that portion of a strand in a first direction that extends over or under two or more strands in a second direction without a binding point. For example, a strand in a first direction may have a binding point with strands in a second direction, then float over 5 adjacent strands in the second direction, then have another binding point with strands in the second direction.

The term "biocompatible" refers to a material that is substantially non-toxic in the in vivo environment of its intended use, and that is not substantially rejected by the patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include without limitation, blood vessels, respiratory ducts, gastrointestinal ducts, such as the biliary duct, intestines, the esophagus, the pericardial cavity, the thoracic cavity, the pericardial cavity, and the like. Accordingly, the terms "endoluminal device" or "endoluminal prosthesis" describe devices that can be placed inside or moved through any such lumen or duct.

The terms "patient," "subject," and "recipient" as used in this application may refer to any animal, particularly humans.

The term "about" used with reference to a quantity includes variations in the recited quantity that are equivalent to the quantity recited, such as an amount that is insubstantially different from a recited quantity for an intended purpose or function.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may constitute an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, and sutures or the like.

Studies show that, with endovascular grafts, the major component contributing to the volume of the delivery system is the graft material. The present invention relates to low profile woven fabrics for implantable medical devices constructed of composite yarns having at least two different materials having different characteristics. The woven fabric comprising of the composite yarn permits fabrication of a device having a lower profile and is capable of delivery through a low profile delivery device of preferably 12 Fr or less. In one embodiment, the woven fabric comprises weaving textile fibers of a composite yarn in a first direction and a second direction, the composite yarn including low denier polyethylene terephthalate terephthalate fibers, commonly known as PET, with low denier polyethylene fibers. Accordingly, a thin woven fabric is achieved that may be used to provide a low profile, durable, biocompatible endovascular graft having the strength and abrasion resistant characteristics of PE with the high biocompatibility of PET.

FIG. 1 illustrates an embodiment of a composite yarn 100 of thread textile strands used in a woven fabric for an endoluminal prosthesis. The composite yarn 100 may be composed of two or more materials and may be natural, synthetic, or manufactured. In some aspects, the composite yarn 100 may be formed by a first material 110 and a second material 114, where the first material has at least one characteristic different than the second material. Preferably, the textile strands are formed from polymers. For example, biocompatible materials from which textile strands can be formed include, but are not limited to, polyesters, such as poly(ethylene terephthalate), and polyethylene. Even more preferably, the textile strands comprise polyethylene terephthalate and ultra-high molecular polyethylene. A preferred commercial example of polyethylene terephthalate especially suited for weaving is Dacron®. A preferred commercial example of ultra-high molecular polyethylene suited for weaving is Dyneema®.

As shown in FIG. 1, the composite yarn comprises a first material 112 and a second material 114 textile strands are twisted together are formed into a twisted rope. The degree of twist required may be determined based on the particular materials used to form the composite yarn 100. In one aspect, the first material 112 has at least one characteristic that is different than the second material. The textile strands of the first material 112 and the textile strands of the second material 114 may be evenly divided based on size in the formed yarn rope 100. The composite yarn preferably has a thickness that is reduced compared to conventional yarns used for woven fabrics. A thickness reduction may be achieved by the use of a smaller denier and/or a reduced density of the weave. In this aspect, textile strands of the first material 112 and the second material 114 of the composite yarn range in size from about 0.1 denier to about 20 denier; preferably between about 5 denier and about 20 denier; even more preferably from about 5 denier to 10 denier.

Accordingly, the first 112 and second material 114 comprising the composite yarn 100 may be chosen such that the sum of each textile strand equals the desired size of the yarn. In some aspects, the composite yarn 110 may range in size from 10 D to 20 D. The size of the first material 112 and the second material 114 forming the composite yarn 100 are desirably formed from low denier textile fibers. In particular, the size of the first material 112 and the second material 114 may range from 5 D to 10 D. In one aspect, the first material 112 comprises polyethylene fibers having a denier of 10 D and the second material 114 comprises polyethylene terephthalate fibers having a denier of 10 D. Thus, the total size of the composite yarn is equal to 20 D. The combination of polyethylene terephthalate fibers and polyethylene fibers provide the woven graft with substantial advantages over conventional graft materials. In particular, the tensile strength of polyethylene allows one to maintain strength characteristics of conventional woven fabric materials in the end product using smaller denier fibers. Further, the composite woven fabric provides geometric advantages by providing the necessary reduction in graft material thickness to achieve smaller delivery system diameters for low profile endovascular graft material. Moreover, the composite woven graft material utilizes the favorable biological response of polyethylene terephthalate as a blood contacting material and subsequent pressure barrier for an endovascular graft.

Figure 2:
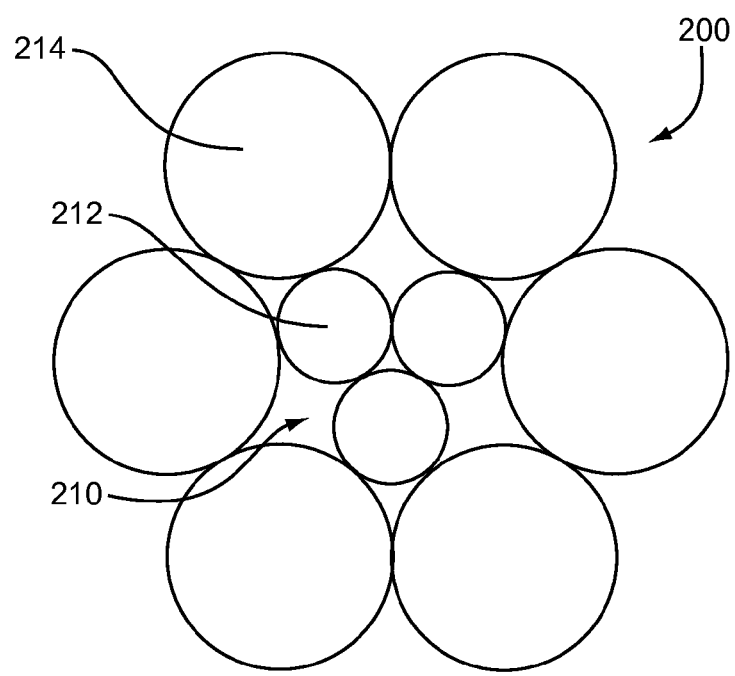
FIG. 2 is an alternative embodiment of composite yarn formed into a rope having an inner core of a first material and an outer surface of a second material.

FIG. 2 illustrates a cross section of an alternative embodiment of a composite yarn 200 used in a woven fabric for an endoluminal prosthesis. The composite yarn includes an inner, central core 210 comprising a plurality of textile strand fibers of a first material 212, and surrounded by a plurality of textile strand fibers of a second material 214, where the first material 212 has at least one characteristic that is different than the second material 214. As shown, the center of the rope comprises three textile strand fibers of the first material 212 surrounded by six textile strand fibers of the second material 214. In other aspects, the number of inner core and outer encompassing fibers may be varied depending on the characteristics desired for the woven graft. For example, the first material 212 may have better tensile strength characteristics and any change in number of textile strand fibers would alter the tensile strength of the composite yarn 200. Additionally, a change in the number of fibers of the second material 214 may have an effect the polymer encapsulation of composite yarn 200 as well. In aspects where the first material 212 and the second material 214 are polyethylene and polyethylene terephthalate, respectively, the composite yarn 200 provides advantageous biological response while providing the requisite mechanical strength advantages. Testing has shown that polyethylene terephthalate forms a high strength bond with other polymers due to its high surface energy/wettability. Thus, the composite yarn 200 may be formed having the tensile strength characteristics of polyethylene while using the polymer adhesion characteristics of polyethylene terephthalate. Additionally, in other aspects, one or more other fibers may be included in the composite yarn 200 to provide the woven fabric with additional desirable characteristics, including, but not limited to, radiopacity and/or shape memory.

Figure 3:
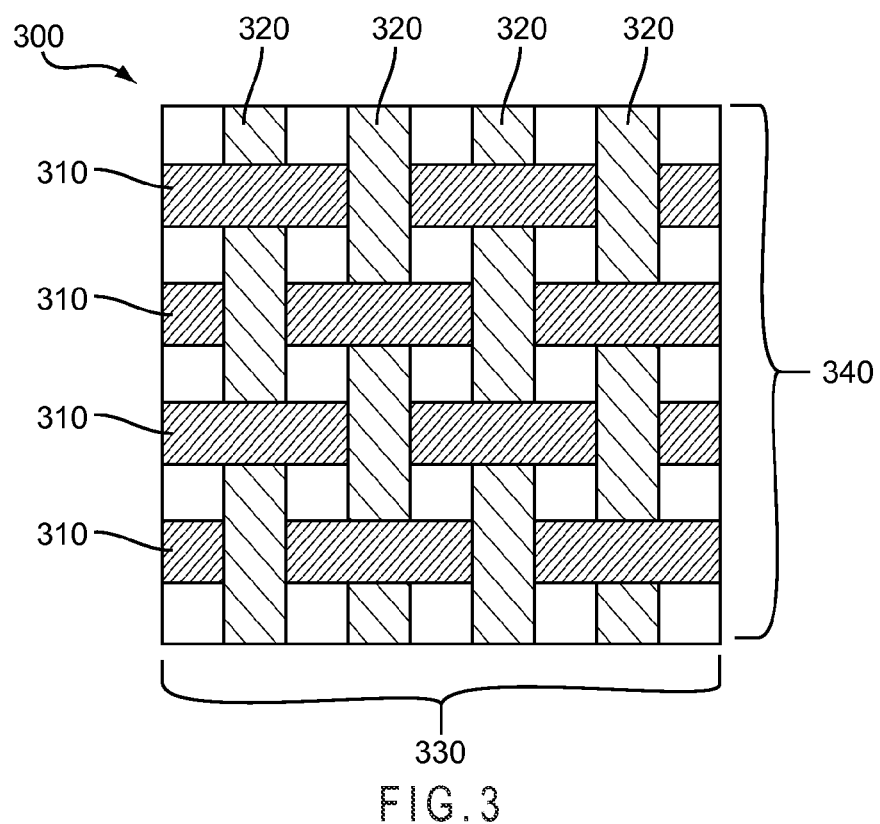
FIG. 3 is a schematic representation of an embodiment of woven fabric weave pattern having composite yarns.

FIG. 3 illustrates an embodiment of a woven fabric 300 having a plurality of composite yarns 310 comprising two or more materials aligned in a first direction 340 interwoven with a plurality of composite yarns 320 comprising two or more materials in a second direction 340. In some aspects, the composite yarns 310, 320 comprise a first material and a second material, where the first material has at least one characteristic different than the second material. The composite yarns 310, 320 are woven, for example, in a plain weave characterized by a regular one-to-one interlacing of strands. That is, the composite yarns aligned in the first direction 330 (e.g., warp direction) move alternatively over and under adjacent strands aligned in a second direction 340 (e.g., weft direction). This plain weave pattern produces the maximum number of binding points, and is thus, a firm, durable weave. However, the woven composite fabric material may comprise any kind of weave. For example, the woven fabric may include, but is not limited to, weaves such as plain weaves, basket weaves, rep or rib weaves, twill weaves (e.g., straight twill, reverse twill, herringbone twill), satin weaves, and double weaves (e.g., double-width, tubular double weave, reversed double weave). The composite woven fabric material may be woven in any suitable manner. For example, the fabric may be woven on a table loom, a floor loom, a jacquard loom, a counterbalance loom, a jack loom, or an upright loom. Desirably, the fabric is woven on a floor loom.

The spacing of the composite yarn textile strands within the weave is expressed in terms of a linear density or line density of strands, and may depend on the denier of the strands. A higher linear density in indicative of a smaller spacing between adjacent strands. During the weaving process to create the composite woven fabric, the sett and pick count are kept constant. The sett may be between about 50 and about 300 ends per inch and the pick count may be between about 3 and about 500 picks per inch. An "end" refers to an individual warp yarn, and a "pick" refers to an individual weft yarn. In some aspects, the composite woven fabric may consist of a balanced weave (e.g. the composite woven fabric has the same number of weft yarns per inch as warp yarns per inch). In other aspects, the composite woven fabric has an unbalanced weave (e.g. the composite woven fabric has an unequal distribution of warp and weft yarns, with one or the other predominating). For example, a composite woven fabric for producing a prosthesis, such as a stent graft, may comprise a plain weave having 150 ends per inch and 250 picks per inch.

During the weaving process, textile strands woven in the weft direction are subjected to much lower tensile loads than textile strands woven in the warp direction. In some aspects, the combination of strength and abrasion resistance of the first material combined with the favorable blood contacting characteristics of the second material help provide a low profile, high strength, abrasion resistant, biologically compatible graft material. Further, the composite yarns 310, 320 provide the woven fabric 300 with sufficient tensile strength to sustain the tensile loads caused in the warp direction during weaving.

Figure 4:
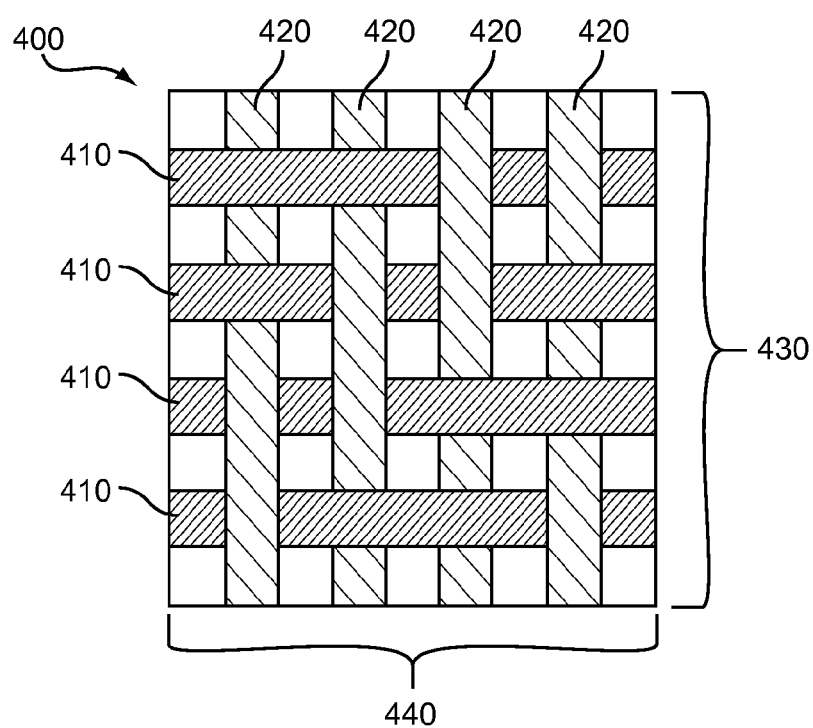
FIG. 4 is a schematic representation of another woven fabric weave pattern having composite yarns.

FIG. 4 discloses an alternative embodiment of the woven fabric 400 having composite yarns 410 comprising two or more materials aligned in a first direction 430 interwoven with a plurality of composite yarns 420 comprising two or more materials in a second direction 440. In some aspects, the composite yarns 410, 420 comprise a first material and a second material, where the first material has at least one characteristic different than the second material. The woven fabric 400 is woven in a 2/2 textile weave pattern. As shown, the binding points of the weft yarns and the warp yarns occur in a diagonal progression known as a wale. This weaving pattern is prepared by passing the textile strands of the composite yarns 410 in the first, or weft, direction over one or more textile strands of the second material in the second, or warp, direction and then under two or more warp threads and so on, with a "step" or offset between rows to create the characteristic diagonal pattern. Floats appear in both the warp direction 430 and the weft direction 440.

Figure 5:
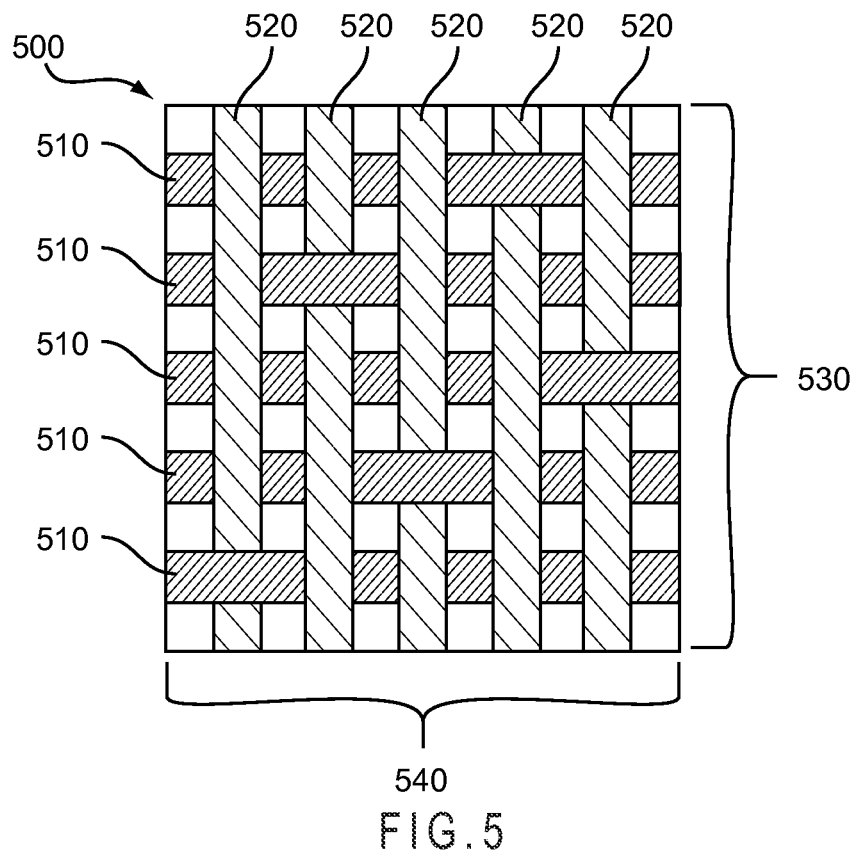
FIG. 5 is a schematic representation of yet another fabric weave pattern having composite yarns.

FIG. 5 depicts a further embodiment of the woven fabric 500 having composite yarns 510 comprising two or more materials aligned in a first direction 540 interwoven with a plurality of composite yarns 520 comprising two or more materials in a second direction 540. In some aspects, the composite yarns 510, 520 comprise a first material and a second material, where the first material has at least one characteristic different than the second material. The composite yarns 510, 520 are woven in a 5-Harness satin weave. As shown, the satin weave is characterized by four or more textile strands of the first material in the first, or weft, direction floating over textiles strands of the second material in the second, or warp direction.

The fabric of the present invention is suitable for use in a variety of implantable or insertable medical devices, for example surgically or endoluminally, of any shape or configuration comprising woven fabric. The medical device may be any device comprising a woven fabric that is introduced temporarily or permanently into the body for the treatment of a medical condition. For example, such medical devices may include, but are not limited to endovascular grafts, stent grafts, balloon catheters, meshes, vascular grafts, stent-graft composites, filters (e.g., vena cava filters), vascular implants, tissue scaffolds, myocardial plugs, valves (e.g., venous valves), various types of dressings, endoluminal prostheses, vascular supports, or other known biocompatible devices.

The medical device may be balloon-expandable or, preferably, self-expanding and may be a bifurcated integrated stent-graft configured for any blood vessel including coronary arteries and peripheral arteries (e.g., renal, superficial femoral, carotid, and the like), a urethral integrated stent-graft, a gastrointestinal integrated stent-graft, or an esophageal integrated stent-graft, for example. Typical subjects (also referred to herein as "patients") are vertebrate subjects (i.e., members of the subphylum cordata), including, mammals such as cattle, sheep, pigs, goats, horses, dogs, cats and humans.

Figure 6:
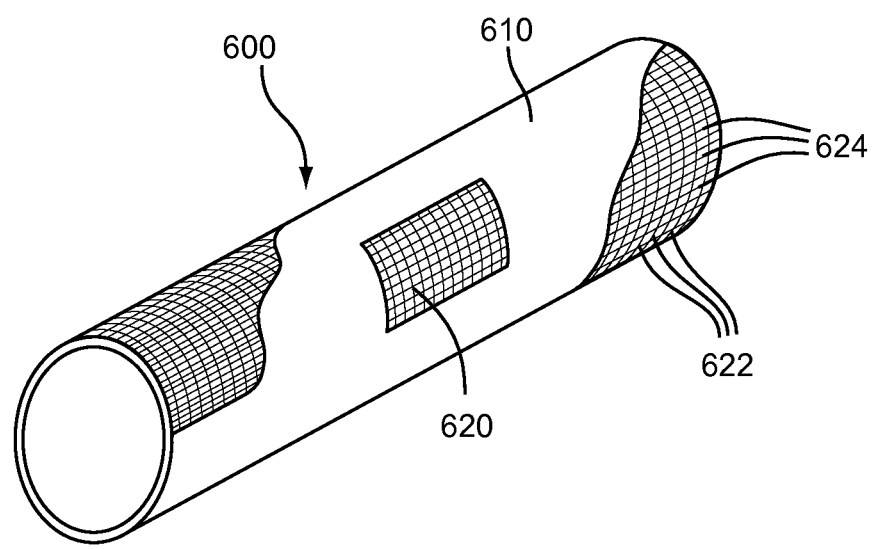
FIG. 6 is a perspective illustration of one embodiment of a medical device comprising a woven fabric having composite yarns.

FIG. 6 is a schematic of a stent graft 600 having a tubular structure 610 and a woven fabric 620. The woven fabric 620 has circumferential strands 622 and longitudinal strands 624, though the strands need not be radial and longitudinal and may have any possible orientation. The circumferential strands 622 and the longitudinal strands 624 may have any suitable weave configuration, such as those shown by FIG. 3-5. Although two dimensional weave patterns are shown, it is possible for the composite woven fabric to have strands woven in a third direction. The stent graft may include stents made from numerous metals and alloys. In one example, the stents comprise a shape-memory material such as a nickel-titanium alloy ("Nitinol"). Moreover, the structure of the stents may be formed in a variety of ways to provide a suitable support structure. For example, one or more stents may be made from a woven wire structure, a laser-cut cannula, individual interconnected rings, or another pattern or design. The stents may be configured in the form of one or more "Z-stents", each of which may comprise a series of substantially straight segments interconnected by a series of bent segments. The bent segments may comprise acute bends or apices. The stents are arranged in a zigzag configuration in which the straight segments are set at angles relative to each other and are connected by a bent segment. However, as noted above, the stents may comprise any suitable configuration and one or more stents may be provided.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. A woven fabric for a low profile implantable medical device consisting of:
   a plurality of textile strands of a composite yarn aligned in a first direction interlaced with a plurality of textile strands of the composite yarn aligned in a second direction; the composite yarn consisting of a combination of a first material and a second material,
   where the textile strands have a size between about 10 denier to about 20 denier, where the first material has at least one characteristic different from the second material, where the first material is ultra-high molecular weight polyethylene and the second material is polyethylene terephthalate, and where the composite yarn consists of a rope having a central core of fibers of the first material surrounded by fibers of the second material.

2. The woven fabric of claim 1, where the textile strands of the composite yarn aligned in the first direction consist of warp yarns, and the textile strands of the composite yarn aligned in the second direction consist of weft yarns.

3. The woven fabric of claim 1, where the composite yarn consists of a twisted rope.

4. The woven fabric of claim 1, wherein the composite yarn has a size of 20 denier.

5. The woven fabric of claim 4, where the composite yarn consists of about 50% of the first material by size and about 50% of the second material by size.

6. The woven fabric of claim 1, wherein the woven fabric has a pick count between about 3 and about 500.

7. The woven fabric of claim 1, where the woven fabric consists of a weave selected from the group consisting of a plain weave, a basket weave, a rep weave, a rib weave, a twill weave, a leno weave, a mock leno weave, a satin weave, a double weave, or a variation thereof.

8. The woven fabric of claim 7, wherein the woven fabric consists of a plain weave.

9. The woven fabric of claim 1, wherein the textile strands aligned in the first direction has at least one float of at least two textile strands aligned in the second direction.

10. A woven fabric suitable for an implantable medical device consisting of:
    a plurality of textile strands of a composite yarn aligned in a first direction interlaced with a plurality of textile strands of a composite yarn in a second direction;
    where the composite yarn consists of polyethylene terephthalate fibers intertwined with ultra-high molecular weight polyethylene fibers, the polyethylene terephthalate fibers and the ultra-high molecular weight polyethylene fibers each having a size of about 10 denier to about 20 denier,
    where the polyethylene terephthalate fibers have at least one characteristic different than the ultra high molecular weight polyethylene fibers, and where the composite yarn consists of a rope having a central core of ultra-high molecular weight polyethylene fibers surrounded by polyethylene terephthalate fibers.

11. The woven fabric of claim 10, where the composite yarn consists of a twisted rope.

12. The woven fabric of claim 10, wherein the composite yarn has a size of 20 denier.

13. The woven fabric of claim 12, where the composite yarn consists of about 50% by size of polyethylene terephthalate fibers and about 50% by size of ultra-high molecular weight polyethylene fibers.

14. A method of producing a woven fabric for an implantable medical device consisting of the steps of:
    providing a plurality of textile strands of a composite yarn to be aligned in a first direction;
    providing a plurality of textile strands of the composite yarn to be aligned in a second direction; and
    weaving the textile strands to produce a woven fabric,
    where the textile strands of the composite yarn have a size between about 10 denier to about 20 denier, and
    where the composite yarn consists of a combination of a first material and a second material and where the first material is ultra-high molecular weight polyethylene and the second material is polyethylene terephthalate, and where the composite yarn consists of a rope having a central core of fibers of the first material surrounded by fibers of the second material.

15. The method of claim 14, where the textile strands of the composite yarn in the first direction are woven to have at least one float of at least two textile strands in the second direction.

16. A woven fabric for a low profile implantable medical device consisting of:
    a plurality of textile strands of a composite yarn aligned in a first direction interlaced with a plurality of textile strands of the composite yarn aligned in a second direction; the composite yarn consisting of a combination of a first material and a second material,
    where the textile strands have a size between about 5 denier to about 20 denier, where the first material has at least one characteristic different from the second material, where the first material is ultra-high molecular weight polyethylene and the second material is polyethylene terephthalate, where the total denier of the composite yarn is 20 denier or less, and where the composite yarn consists of a rope having a central core of fibers of the first material surrounded by fibers of the second material.

* * * * *